United States Patent [19]

Taimisto et al.

[11] Patent Number: 5,351,693
[45] Date of Patent: Oct. 4, 1994

[54] ULTRASOUND PROBE FOR USE WITH TRANSPORT CATHETER AND METHOD OF MAKING SAME

[75] Inventors: Miriam H. Taimisto, Sierra Madre; David L. Swendson, Garden Grove, both of Calif.; Lawrence J. Busse, Littleton, Colo.; Robert Skidmore, Bristol, United Kingdom

[73] Assignee: Baxter International Inc., Deerfield, Ill.

[21] Appl. No.: 137,381

[22] Filed: Oct. 13, 1993

Related U.S. Application Data

[63] Continuation of Ser. No. 865,163, Apr. 8, 1992, abandoned, which is a continuation-in-part of Ser. No. 790,724, Nov. 8, 1991, Pat. No. 5,246,016.

[51] Int. Cl.⁵ ............................................. A61B 8/06
[52] U.S. Cl. ............................. 128/662.06; 73/861.25
[58] Field of Search ................. 128/661.07–661.10, 128/662.06; 73/861.25

[56] References Cited

U.S. PATENT DOCUMENTS

| | | | |
|---|---|---|---|
| 3,123,066 | 3/1964 | Brumley | 128/2 |
| 3,136,310 | 6/1964 | Meltzer | 128/2 |
| 3,430,625 | 3/1969 | McLeod, Jr. | 128/2.05 |
| 3,461,856 | 8/1969 | Polanyi | 128/2 |
| 3,499,435 | 3/1970 | Rockwell et al. | 128/2.05 |
| 3,807,390 | 4/1974 | Ostrowski et al. | 128/2.05 |
| 3,866,599 | 2/1975 | Johnson | 128/2 |
| 3,981,299 | 9/1976 | Murray | 128/349 |
| 4,050,450 | 9/1977 | Polanyi et al. | 128/2 |
| 4,259,870 | 4/1981 | McLeod et al. | 128/662.06 X |
| 4,431,936 | 2/1984 | Fu et al. | 310/335 |
| 4,582,067 | 4/1986 | Silverstein et al. | 128/663 |
| 4,733,669 | 3/1988 | Segal | 128/662.06 X |
| 4,757,821 | 7/1988 | Snyder | 128/660 |
| 4,770,185 | 9/1988 | Silverstein et al. | 128/661.08 |
| 4,802,490 | 2/1989 | Johnston | 128/661.08 |
| 4,869,263 | 9/1989 | Segal et al. | 128/692 |
| 4,947,852 | 8/1990 | Nassi et al. | 128/662.06 |
| 4,967,753 | 11/1990 | Haase et al. | 128/662.06 |
| 4,991,588 | 2/1991 | Pflueger et al. | 128/662.06 |
| 4,994,396 | 2/1991 | Lefkowitz et al. | 436/136 |
| 5,025,778 | 6/1991 | Silverstein et al. | 128/4 |
| 5,174,295 | 12/1992 | Christian et al. | 128/662.06 |

FOREIGN PATENT DOCUMENTS 0303756 2/1989 European Pat. Off. .
WO89/00023 1/1989 PCT Int'l Appl. .

OTHER PUBLICATIONS

"Usefulness of Doppler Catheters in Assessment of Coronary Artery Blood Flow", Richards, et al., *Cardiac Doppler Diagnosis*, 1983, pp. 91–97.
"High Speed Solution of 2nd Order Curves With Special Application to Planar Sections of Blood Vessels", Martin, *Computer Programs in Bio Medicine*, 1981, pp. 45–60.
"Stroke Volume Measurement with an Ultrasonic Catheter Tip System", Martin et al., *Ultrasound in Medicine*, vol. 3A, 1977, pp. 23–39.
"An Ultrasonic Catheter for Intravascular Measurement of Blood Flow: Technical Details", Martin et al., *IEEE Transactions on Sonics and Ultrasonics*, Nov. 1980, vol. SU–27, No. 6, pp. 277–286.
"An Ultrasonic Catheter Tip Instrument for Measuring Volume Blood Flow," Martin et al., *Ultrasonics Symposium Proceedings*, 1975 IEEE Cat. #75 CHO 994–4SU, pp. 13–17.
"Continuous Measurement of Cardiac Output with an Ultrasonic Catheter", Martin, *Cardiac Doppler Diagnosis*, 1983, Chapter 9, pp. 81–90.

*Primary Examiner*—Francis Jaworski
*Attorney, Agent, or Firm*—Bruce M. Canter

[57] ABSTRACT

A probe for use within a catheter is disclosed. The probe transducer portion is constructed of a crystal hollow cylinder with an inside lead attached to the inner surface of the crystal cylinder. One end of the outside lead is positioned close to the outer surface, in a plane tangential to the outer surface, and is coupled to the outer surface of the crystal cylinder by a thin sputtered layer of conductive material. The probe transducer also includes a layer of acoustically absorbing material on the proximal end of the crystal, and layer of acoustically coupling material on the distal end of the crystal cylinder. The transducer element simultaneously generates an axially oriented signal beam at one frequency and a radially oriented signal beam at 2 different frequency. The signal beams are analyzed to calculate the blood flow area and the blood flow velocity, the product of which is the blood flow rate.

7 Claims, 4 Drawing Sheets

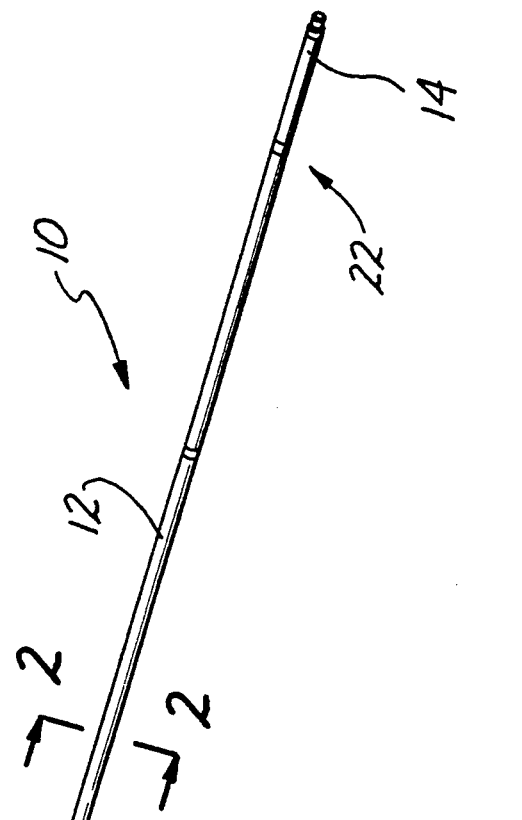
Fig. 9
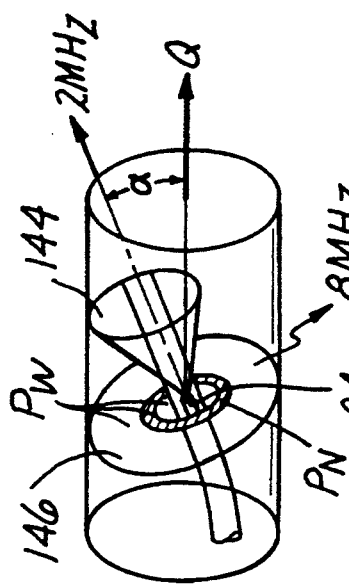
Fig. 1
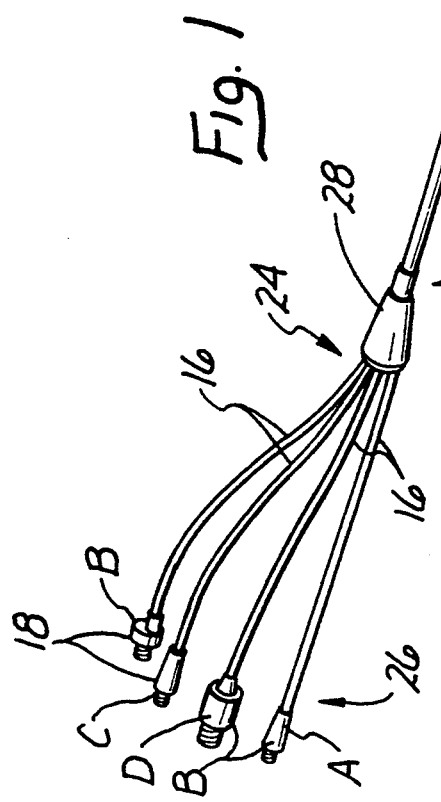
Fig. 2
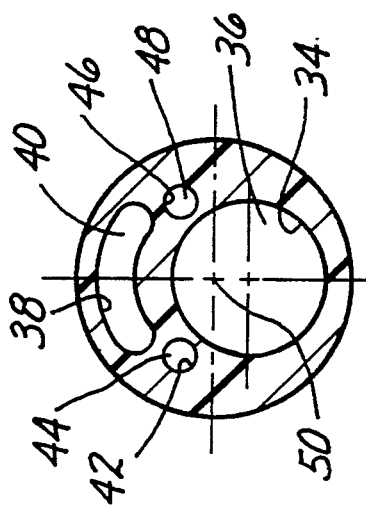

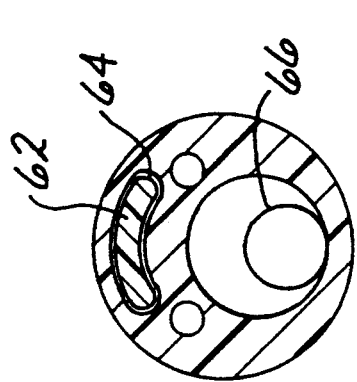
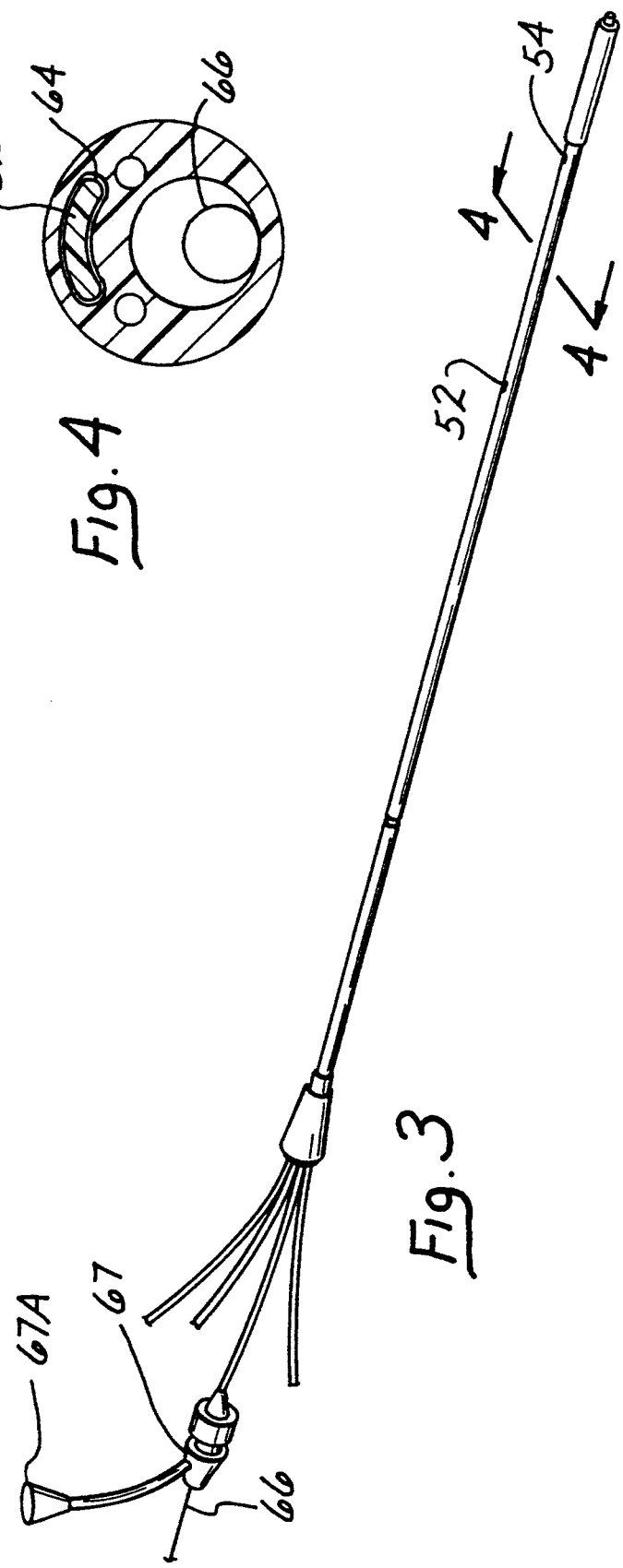
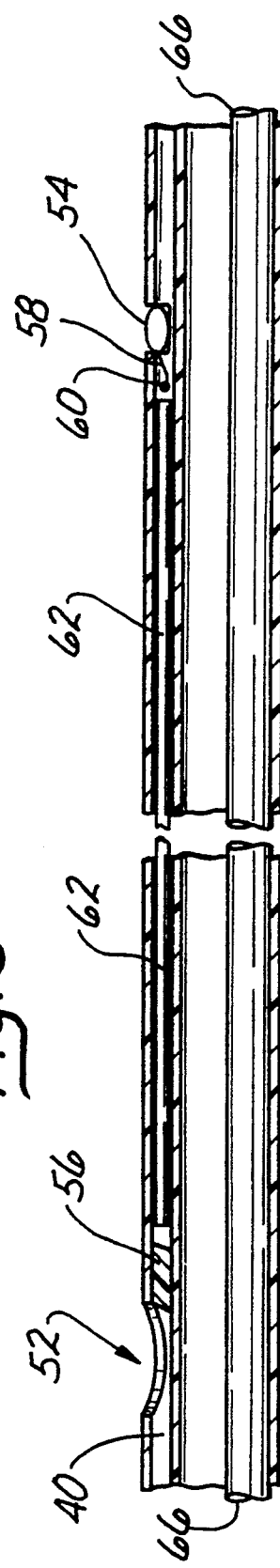
Fig. 3
Fig. 4
Fig. 5

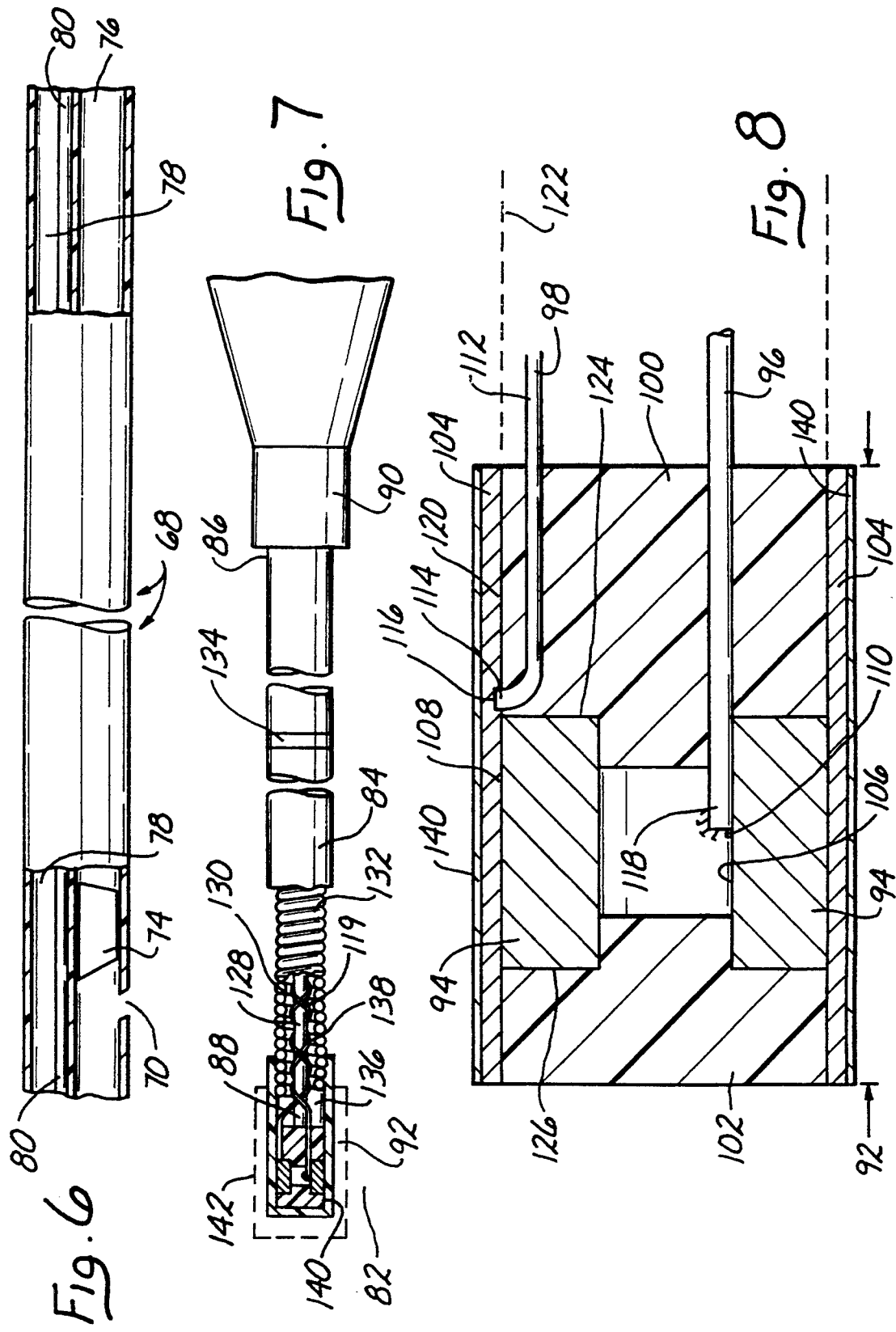

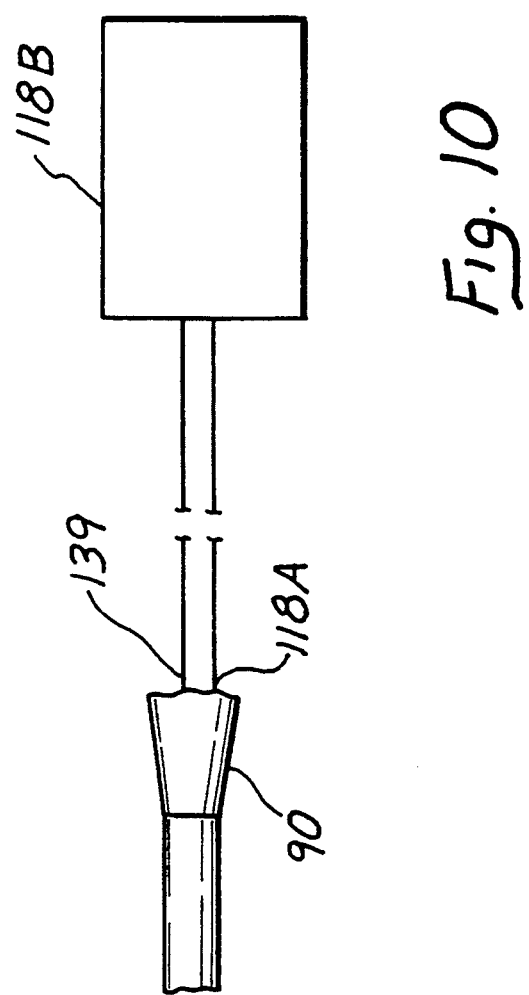

& #x20;# ULTRASOUND PROBE FOR USE WITH TRANSPORT CATHETER AND METHOD OF MAKING SAME

Related Application Data

This is a continuation, of commonly owned, co-pending U.S. application Ser. No. 07/865,163, filed on Apr. 8, 1992, and now abandoned which is a continuation-in-part of commonly owned, co-pending application, Ser. No. 07/790,724, filed on Nov. 8, 1991, now U.S. Pat. No. 5,246,016.

BACKGROUND OF THE INVENTION

1. Field of the Invention

The present invention relates to an improved ultrasound probe and method of making an ultrasound probe for use in connection with a multi-lumen transport catheter. The present invention more particularly relates to an improved ultrasound probe that allows for more accurate ultrasound readings and has a relatively small outer diameter, such that it can be used in connection with an improved catheter which can accept various probes for sensing biological conditions and parameters and which allows high fluid flow rate for introducing fluids irrespective of the presence of sensing instruments in the catheter, thereby reducing the risk of patient complications.

2. Description of Related Art

Numerous catheters exist for sensing, diagnosing and treating various biologic conditions. For example, there are cardiac catheters used for angioplasty, for measuring cardiac output, such as thermodilution catheters, pulmonary artery wedge pressure monitors, blood flow monitors and temperature monitors. In use, a transport catheter is initially introduced into an appropriate vessel or body cavity. In the case of a thermodilution catheter, for example, the transport catheter may be introduced into an appropriate vein. Thereafter, the thermodilution catheter is inserted and passed through the right atrium and ventricle and out to the pulmonary artery. After the catheter is properly positioned and the balloon inflated, various readings can be taken of left heart pressure, for example, and pulmonary artery temperature. The same measurements may be taken a number of times while the catheter is in place. However, if the patient's condition changes and requires other measurements or diagnosis, or additional information is desired, such as may be required in view of the results obtained by the thermodilution measurements, the thermodilution catheter must be removed and substituted with a different catheter for such measurements. The subsequent catheter exchange increases the possibility of infection through the introduction of a second catheter and increases the probability of other problems such as venous puncture.

Another problem with frequent catheter exchange is that only physicians are authorized to remove and replace catheters and probes in the patient's body. However, after a physician has inserted and positioned the catheter in the patient's body, a trained nurse is permitted to insert, position, and replace probes within the catheter, since the probe does exit the catheter. Therefore, it is desirable to use a transport catheter in connection with a probe, such that the probe can be used within the transport catheter without the removal and replacement of the transport catheter.

In the past, multi-lumen catheters were designed wherein the catheter body was divided into circular sections of similar size or substantially triangular sections to form the separate lumens. These catheters were generally too small to accept sensing probes and one or more of the lumens of such catheters occasionally become constricted at the seal of the transport catheter. A further disadvantage of these multi-lumen catheters becomes apparent if an ultrasound probe was to be used within one of the lumens of the catheter in order to obtain diagnostic readings. In this case, the similar sized lumens surrounding the probe-carrying lumen contain relatively large amounts of air space that cause undesirable attenuation of the ultrasonic signal.

Undesirable signal attenuation is also caused by the transducer design of the prior art ultrasound probes. For example, ultrasound probe transducers may be formed of crystal material, having two leads attached to the crystal material. The first lead is connected to the inner surface of the crystal material, and the second lead is connected to the outer surface of the crystal material. The location of the second lead on the crystal material causes a "dead" spot in the attenuation pattern of the ultrasound signal. Therefore, the ultrasound probe does not provide as accurate of a reading as desired. Also, the attachment of the second lead to the outer surface of the crystal cylinder causes the outer diameter of the ultrasound probe to increase, making it difficult to fit the ultrasound probe within the transport catheter. Therefore, a need exists for an ultrasound probe having a relatively small outer diameter, and which does not produce dead spots in the attenuation pattern of the ultrasound signal.

In patients undergoing major surgery or suffering from serious illness, there is an acute need for a continuous blood flow measurement, as compared to an intermittent blood flow measurement. Therefore, ultrasonic transducer probes have been designed to continuously measure cardiac blood flow.

A known method of calculating blood flow is to multiply the area of the blood flow times the velocity of the flow. Methods have been developed for using ultrasound transducers to calculate the area and to calculate the blood flow velocity. For example, it is known to use echo patterns to determine the cross-sectional area of a blood vessel, and to use a Doppler technique to determine blood flow velocity.

However, in order to measure both cross-sectional area and velocity, two separate and distinct ultrasound transducer elements were used. A first transducer element was used to obtain measurements of the flow area, and a second transducer element was used to obtain measurements of the flow velocity. For example, in one method, several transducer elements are located at the catheter tip. A first plurality of transducer elements are activated and used to calculate the cross-sectional area of the vessel perpendicular to the catheter tip by echo methods. With the same catheter, a second distinct annular transducer element is activated to determine the velocity of the blood which flows perpendicular to the cross-sectional area. The velocity is determined by using the Doppler principle, wherein the Doppler shift created by the movement of the blood cells is analyzed. The product of the two measurements provides the blood flow measurement.

Another method of determining blood flow includes a method wherein the transducer generates a single large uniform cone-shaped beam which extends forwardly into the pulmonary artery. However, in this method, only a single cone-shaped beam is analyzed, and a radially-oriented beam is not utilized to determined the cross-sectional area of the artery.

With many of the known ultrasound probes, the probe must be axially aligned within the blood vessel and blood flow in order to provide an accurate reading. If the probe is not properly aligned, the angle of incidence between the probe axis and the blood flow adversely affects the accuracy of the ultrasound probe measurements. Therefore, a need exists for an ultrasound probe with a single transducer element that can generate a radially oriented signal beam and a forwardly oriented beam simultaneously, and which is not affected by the angle between the axis of the transducer and the blood flow.

There is also a need for an improved catheter which can accept an ultrasound probe, and which also, simultaneously, allows for high fluid flow for fluids to be introduced into the body, as well as the introduction of relatively viscous fluids. Additionally, a need exists for a multi-lumen catheter that minimizes the sizes of the lumens which might contain ultrasonic wave attenuating air in lumens adjacent an instrument containing lumen.

SUMMARY OF THE INVENTION

One object of the present invention is to provide an ultrasound probe that provides increased accuracy in ultrasound readings by reducing dead spots in the sound wave attenuation pattern.

Another object of the present invention is to provide an ultrasound probe with a relatively small outer diameter.

A further object of the present invention is to provide an ultrasound probe that can be used in connection with a multi-lumen transport catheter.

Another object of the present invention is to provide a transport catheter that provides a plurality of lumens for accepting various sequential probes through at least one of the lumens without requiring the insertion and removal of a different catheter with each probe.

Yet another object of this invention is to provide a transport catheter with a plurality of lumens that allows for an increased accuracy in ultrasound readings by minimizing the attenuation of the signal caused by the quantity of air space in the surrounding lumens.

Still another object of this invention is to provide an ultrasound probe with a single transducer element that can generate a radially oriented signal beam and a forwardly oriented beam substantially simultaneously.

Yet another object of this invention is to provide an ultrasound probe with a single transducer element for measuring blood flow that is not affected by the angle of incidence between the axis of the transducer and the blood flow.

These and other objects are achieved through an ultrasound probe for use within a transport catheter, comprising a probe body having a distal and a proximal end, and a transducer portion attached to the probe body distal end. The transducer portion of the probe comprises a piezoelectric crystal in the form of a hollow cylinder having a distal end and a proximal end, and further defining an inner surface and an outer surface. An inside lead is coupled to the inner surface of the crystal cylinder, and an outside lead is coupled to the outer surface of the crystal cylinder. The outside lead has a first and a second end, wherein the first end is coupled to the outer surface of the crystal cylinder by a conductive material, while a substantial portion of the outside lead remains within the diameter defined by the crystal cylinder. The preferred transducer portion includes a layer of acoustically coupling material deposited adjacent the distal end of the crystal and a layer of acoustically absorbing material deposited adjacent the proximal end of the crystal cylinder.

The transducer portion alternately generates a radially oriented signal beam at a first frequency, and then generates a forwardly oriented signal beam at a second frequency. The signal beams are used to calculate cross-sectional area and blood flow velocity, respectively, which are then used to calculate blood flow.

The probe is preferably designed for use within a catheter of the present invention comprising a catheter body having an outer edge with an outer dimension and having a proximal end and a distal end. The body also includes walls defining, in transverse cross-section, a plurality of lumens extending longitudinally substantially through the catheter body including a first wall defining a first lumen having a first transverse dimension approximating about half of the dimension of the catheter body. A second wall defines a curved lumen wherein the lumen occupies at least a quarter of an arc around the catheter body.

The above described objects and other objects of the present invention will now become apparent from a review of the drawings and the following description of the preferred embodiments.

BRIEF DESCRIPTION OF THE DRAWINGS

FIG. 1 is a perspective view of the transport catheter of the present invention.

FIG. 2 is a cross-sectional view of the transport catheter of the present invention taken along line 2—2 of FIG.1.

FIG. 3 is a perspective view of a catheter according a further embodiment of the present invention showing a probe and an injectate port.

FIG. 4 is a transverse cross-sectional view of the catheter of FIG. 3 taken along line 4—4.

FIG. 5 is a longitudinal cross-sectional view of a portion of the catheter of FIG. 3.

FIG. 6 is a partial segmented side-sectional view of a catheter according to a further embodiment of the present invention.

FIG. 7 is partial segmented side-sectional view of an ultrasound probe of the present invention.

FIG. 8 is a side-sectional view of a transducer of the ultrasound probe of the present invention.

FIG. 9 is a representational view of the ultrasound probe with a single transducer element generating radially and forwardly oriented signal beams within a blood vessel.

FIG. 10 is a schematic representation of the signal source for the ultrasound probe.

DETAILED DESCRIPTION OF THE PREFERRED EMBODIMENTS

Referring now to FIG. 1, a catheter 10 for accepting probes and for introducing fluid through the catheter and into a body cavity is shown which allows numerous procedures to be done using a single catheter and which reduces the likelihood of injury to the patient. In one preferred embodiment, the catheter 10 is primarily comprised of a catheter body 12, an inflation balloon 14, a plurality of extension tubes 16, and a plurality of threaded hubs 18. The catheter body 12 has a proximal end 20 and a distal end 22. The inflation balloon 14 is mounted to the catheter body 12 at the distal end 22 of the catheter body 12 as would be known to one skilled in the art. Each of the extension tubes 16 has a respective first end 24, which is coupled to a corresponding one of a plurality of lumens (shown in FIG. 2) in the catheter body 12 at the catheter body proximal end 20 at a backform 28. The extension tubes 16 provide access to each of the respective lumens. The extension tube corresponding to the first lumen, described more fully below, also includes graduations on the outside of the tube to indicate the depth of insertion of any probe or instrument passed along the first lumen. The second end 26 of each of the extension tubes 16 is coupled to a respective one of the plurality of threaded hubs 18. The threaded hubs 18 each have a luer taper common in the art for connecting suitable instruments, such as probe connectors, an inflation device for the inflation balloon and an injection device for the injectate lumen described more fully below.

Referring now to FIG. 2, a cross-sectional view of the catheter body 12 is shown taken at an approximate mid-point of the catheter body. A plurality of walls within the catheter body 12 define the respective plurality of lumens. A first wall 34 defines a first lumen or probe lumen 36. The cross-sectional configuration of the probe lumen 36 is preferably circular, and has a diameter in the preferred embodiment of approximately half the diameter of the cross-section of the catheter body 12. A second wall 38 defines a second lumen or an injectate lumen 40. In the preferred embodiment shown in FIG. 2, the cross-section of the injectate lumen 40 is crescent-shaped. A suitable size for the second lumen is one where it occupies at least a quarter of an arc around the cross-section of the catheter body 12. A third wall 42 defines a third, inflation lumen 44, in cross-section preferably circular, and a fourth wall 46 defines a fourth lumen 48, also preferably circular.

The probe lumen has a large cross-sectional area and preferably occupies a significant portion of the cross-sectional area of the catheter so that the catheter can accept as many different types and configurations of probe as possible and to permit a wide variety of tasks or procedures without having to remove the catheter. The probe lumen also accepts the improved ultrasound probe of the present invention herein. The probe lumen is also preferably large enough to permit fluid flow within the lumen even while a probe or other element is in the probe lumen. This allows simultaneous instrument sensing and pressure monitoring or introduction of fluid such as pharmaceutical through the probe lumen, even with concurrent introduction or withdrawal of fluid through the injectate lumen 40. In this manner, removal of the probe is not required before injectate can be introduced or blood withdrawn through the probe lumen. Fluid pressure can also be monitored even while a probe is in place in the lumen 36. For example, the lumen 36 is capable of accepting hemoglobin oxygen saturation probes, pacing probes, cardiac output probes, right heart ejection fraction probes, right heart ejection fraction with hemoglobin oxygen saturation probes, hemoglobin pH probes, and high fidelity pressure monitoring probes. A preferred probe configuration is circular in external dimension. In one preferred form of the invention having the four lumens as described, a 7½ French catheter has a 0.056 inch diameter probe lumen and the probes are preferably around 0.042 inches in diameter.

The advantage of the probe substitution feature of the probe lumen 36 is apparent from a description of the use of the catheter 10. In use, the catheter body 12 is first inserted and properly positioned in the body by a physician. A selected probe is then inserted through the probe lumen 36 of the catheter body 12, by either a physician or a nurse, and the desired procedure is carried out. Thereafter, another type of probe measurement may be required such as where the patient's condition changes. The first probe is then removed from the catheter body 12, leaving the catheter body 12 in place, and a second probe is inserted through the probe lumen 36 of the catheter body 12 in order to accomplish a different probe function. The insertion and removal of the catheter body with each type of probe is avoided, and a nurse is permitted to insert and remove each of the probes without requiring the physician's presence. As a result, there is significantly less risk to the patient of infection from the repeated insertion and removal of catheters, as well as less risk of venous puncture or other problems. Moreover, because the insertion and removal of the probes can be accomplished by a nurse, the insertion and removal process of the probes is more convenient and efficient while the physician may otherwise be occupied.

The large cross-sectional area of the injectate lumen 40 allows for a high fluid flow rate through the lumen, and also accommodates the flow of relatively viscous fluids. Therefore, the second lumen 40 is well-suited for procedures requiring either high fluid flow rates or the introduction of relatively viscous fluids. The second, injectate lumen 40 is even more significant where fluid must be introduced or withdrawn at the same time the probe lumen is being used. The cross-section of the injectate lumen 40 is preferably crescent-shaped, with the cross-section of the lumen covering or extending around at least a quarter arc of the catheter body cross-section. The crescent shape allows for maximum fluid flow area within the catheter body 12 without interfering with the first lumen 36.

The third lumen 44 is preferably used for inflating and deflating the inflation balloon 14 to properly position the catheter, for example where the catheter is used as a thermodilution catheter. The fourth lumen 48 is preferably used for instrumentation, such as for passing thermistor wires or the like along the catheter to a point where a sensing device is located in the catheter.

The catheter body 12 of the present invention is preferably formed by any of several well known extrusion methods. The catheter body 12 may be fabricated from any of a variety of suitable materials, including, but not limited to, flexible polyvinyl chloride (PVC), polyurethane, nylon, or polypropylene. The catheter body 12 is also preferably coated with heparin.

In the preferred embodiment described herein, the catheter body 12 has an outer diameter of 0.101 inches centered on the central axis 50 of the catheter. The total cross-sectional area of the catheter body 12 is therefore approximately 0.008 square inches. The first lumen 36 preferably is circular with a diameter of 0.056 inches and includes within it the central axis 50. The cross-sectional area of the first lumen 36 is therefore approximately 0.0024 square inches, which equates to approximately thirty percent of the catheter body cross-sectional area. The cross-sectional area of the crescent-shaped second lumen 40 is approximately 0.0016 square inches, which is approximately twenty percent of the total cross-sectional area of the catheter body 12. The largest distance between oppositely arcing surfaces in the crescent shape is about 0.024 inches and the radius of curvature of the ends of the injectate lumen is about 0.010 inches. To optimize the available area that can be used for fluid flow, the injectate lumen in the preferred embodiment is symmetrically placed above the probe lumen and centered so that an imaginary vertical plane (vertical when viewing FIG. 2) through the central axis 50 and the central axis of the probe lumen bisects both the probe lumen and the injectate lumen. It should be understood, however, that where one or the other of the third or fourth lumens is omitted, the injectate lumen may be formed asymmetrically relative to a line through the central axis 50 and the central axis of the probe lumen. The third lumen 44 and the fourth lumen 48 are both preferably circular, and have a diameter of approximately 0.012 inches. Therefore, the cross-sectional areas of the third lumen 44 and the fourth lumen 48 are each approximately 0.0001 square inches, which equates to approximately one and one-half percent of the total cross-sectional area of the catheter body 12. The smallest dimension from any of the lumens radially to the outer edge of the catheter body is preferably 0.007 inches. The thickness of any wall between lumens is preferably at least 0.007 inches. The dimensions of the catheter body 12 and lumens given are preferred, but they are exemplary only of the preferred embodiment of the invention.

It should be understood that the cross-sectional configuration shown in FIG. 2 is preferred, and extends in the preferred embodiment substantially the entire length of the catheter. However, it should also be understood that the inflation lumen 48 terminates at the inflation balloon 14. It should also be understood that the injectate lumen may open at an injectate port 52 through the outer catheter wall at a suitable location near the distal end 22 along the length of the catheter body (FIG. 3). Where the catheter has an overall usable length of 110 centimeters, the injectate port 52 is typically located about 30 centimeters proximal of the distal end of the catheter, a standard distance for a thermodilution catheter. A thermistor 54 is exposed to the outside of the catheter approximately 4 centimeters proximal of the distal end.

Considering the distal-most portions of the catheter in more detail (FIGS. 4 and 5), fluid flow out the injectate port is created by placing an injectate lumen plug 56 in the injectate lumen 40. The plug 56 has a general transverse cross-section conforming to that of the injectate lumen and is sealed in place by a suitable biocompatible filler. The thermistor 54 is potted in an opening formed in the outer catheter surface. Preferably, the thermistor is potted in the injectate lumen since the injectate lumen downstream of the plug 56 is otherwise unused. Thermistor wires 58 from the fourth lumen 48 pass into the injectate lumen 40 through a cross-over 60 from the fourth lumen.

In order to reduce the volume of air in the unused and therefore vacant portion of the injectate lumen, namely the portion of the injectate lumen distal of the plug 56, a crescent shaped insert or rod 62 is inserted in the injectate lumen and fixed with a suitable adhesive 64 between the plug 56 and the cross-over 58. The rod is preferably formed from the same material as the catheter and preferably to provide the same flexibility as the catheter without the plug. A probe 66 is shown in FIGS. 4 and 5 and can be made from plastic, metal, plastic coated metal, composites or other suitable materials used in manufacturing probes, sensors or other instrumentation.

A hemostasis valve 67 is also shown in FIG. 3 through which the probe passes into the extension tube. An injection port may also be connected to the valve 67 through an appropriate stopcock, shown schematically at 67A, to which may be connected a conventional pressure sensor device, a fluid injection device, and the like.

The orientation of the lumens within the catheter body 12 accommodates the four lumens with the probe and injectate lumens having a relatively large cross-sectional area. As a result, the cross-sectional areas of the third and fourth lumens remain relatively small. In use, the probe and injectate lumens are filled with a liquid, with only the third and fourth lumens containing any appreciable air space. The relatively small quantity of air space in the third and fourth lumens minimizes undesirable attenuation of ultrasonic signals when an ultrasound probe is used within the probe lumen 36. Therefore, an ultrasound probe used in the probe lumen of the preferred embodiment produces a more accurate result.

The accuracy of the ultrasound probe readings within the transport catheter is also increased when an ultrasound probe 82 of the present invention is used. The ultrasound probe 82 is shown in detail in FIG. 7. The use of the ultrasound probe 82 within the first probe lumen 36 allows the nurse or physician to reposition the probe 82 until it is properly positioned, without causing unnecessary tissue or vascular damage. Moreover, as discussed above, the physician is not required to position the probe within the transport catheter, because a nurse is permitted to replace probes within the catheter. Therefore, the placement of the probe within the catheter body allows for more convenient and less traumatizing replacement and repositioning of the probe.

Referring now to FIG. 7, an ultrasound probe 82, according to one aspect of the present invention, comprises a probe body 84 having a proximal end 86 and a distal end 88, a connector 90, and a transducer portion 92. The connector 90 is coupled to the probe body proximal end 86, and the transducer portion 92 is connected to the probe body distal end 88. The connector 90 is of the type known in the art for use with ultrasound probes.

The transducer portion 92 of the probe is best shown in FIG. 8. In the preferred embodiment, the transducer portion 92 is comprised of a ceramic piezoelectric crystal in the form of a hollow cylinder 94, an inside lead 96, an outside lead 98, an acoustically absorbing layer 100, an acoustically coupling layer 102, and a thin sputtered layer 104. The hollow crystal cylinder 94 defines an inner surface 106, an outer surface 108, a proximal end 124, and a distal end 126.

In manufacturing process of the transducer portion 92, the crystal cylinder 94 if formed by extruding or molding a crystal cylinder of a predetermined length. The inner surface and the outer surface of the extruded crystal cylinder is then plated with nickel or another type of conductive material in order to improve the conductivity between the crystal cylinder and the leads. The extruded crystal cylinder is then cut into approximately 0.027 inches in length in order to form the crystal cylinder 94 for the transducer portion 92.

A first end 118 of the inside lead 96 is then coupled to the inner surface 106 of the crystal cylinder with an electrically conductive material. Preferably, the inside lead first end 118 is coupled to the cylinder inner surface 106 by a silver conductive epoxy 110. The second end 118A of the inside lead 96 is coupled to the probe driving circuit 118B (FIG. 10) through the connector 90 in the conventional manner. A central portion 119 of the inside lead 96 extends through the probe body 84.

The cylinder 94, with the attached inside lead 96, is then temporarily placed in a tube-shaped casting form or mold 142. The outside lead 98 is bent at a ninety degree angle to form an L-shape. It should be noted that various shapes of the outside lead may function in the same manner. However, for purposes of reference, the L-shaped lead is used to describe the preferred embodiment. The L-shaped lead is defined by a long leg 112 and a short leg 114. The short leg 114 of the L-shape ends at the first end 116 of the lead 98. When the crystal cylinder 94 is positioned in the casting form, the first end 116 of the outside lead 98 is placed in close proximity to the outer surface 108 of the crystal cylinder 94, and in an imaginary plane 120 substantially tangential to the outer surface 108 of the crystal cylinder. In this position, the long leg 112 of the L-shaped lead 98 then extends toward the probe body 84, and is located within the imaginary cylindrical shape 122 defined by the outer surface diameter of the crystal cylinder 94. Therefore, preferably, no portion of the outside lead 98 extends outside of the boundaries of the outer diameter of the crystal cylinder 94.

The outside lead includes a central portion 138, which is the portion of the lead between the first and second ends. The central portion 138 extends continuously along the plane of the long leg 114 of the L-shape. Thus, the central portion 138 extends through the probe body 84. A second end 139 (FIG. 10) of the outside lead 98 is coupled to the probe driving circuit 118B through the connector 90 in the conventional manner.

The layer of acoustically coupling material 102 is then deposited adjacent the distal end 126 of the cylindrical crystal 94. The acoustically coupling layer 102 is also referred to as the matching layer. Preferably, an epoxy material is used for the matching layer. The epoxy material is selected so as to be acoustically coupled with the transducer. As shown in FIG. 8, the acoustically coupling layer 102 is formed in a plug shape, and may extend into a portion or all of the center of the crystal hollow cylinder.

The purpose of the acoustically coupling layer 102 is to generate a solid cone forwardly oriented ultrasound wave velocity beam 146 (shown in FIG. 9) from the transducer 92. The sound wave velocity beam generated by the transducer without the acoustically coupling layer resembles a first cone with a second hollow cone portion in the center of the first cone. However, with the acoustically coupling layer, the second hollow cone is filled with sound waves, and the velocity beam 144 becomes a solid cone. The purpose and function of the forwardly oriented solid cone ultrasound wave velocity beam is described in more detail herein. Therefore, the acoustically coupling layer 102 allows for more accurate readings from the transducer.

The layer of acoustically absorbing material 100 is then deposited adjacent a proximal end 124 of the crystal cylinder. Preferably, an epoxy material doped with approximately eighteen to twenty-six percent rubber powder, such as HYCAR (TM) type 1422 polymer, available from Zeon Chemicals, Inc., Illinois, sifted through a 100 mesh screen, is used so as to act as a sound absorber. This layer of epoxy is also known as the backing layer of the transducer portion 92. The acoustically absorbing layer 100 is preferably formed in a plug shape, and may extend into a portion or all of the center of the hollow crystal cylinder 94.

At this point, the transducer portion is removed from the casting form 142. The matching layer, or acoustically coupling layer is then ground down to a predetermined length, so as to enable the transducer to produce a ¼ or ¾ ultrasound wave length signal.

After the matching layer 102 is ground, the sputtered layer 104 is applied in order to make the electrical connection between the crystal cylinder outer surface 108 and the outside lead 98. The thin sputtered layer 104 of conductive material, preferably gold or chromium, is sputtered along the plane 120 defined by the crystal cylinder outer surface 108 and the outside lead first end 116. Once the layer 104 of gold or chromium is applied, the outside lead 98 is then conductive with the crystal cylinder outer surface 108. Therefore, when current is applied to the leads 96, 98, current will flow from the inner surface 106 of the crystal to the outer surface 108 of the crystal or vice versa. Moreover, because the outside lead 98 is not directly attached to the outer surface 108 of the crystal cylinder, the dead spots in the ultrasound wave pattern are eliminated, and the probe 82 retains its relatively small outer diameter.

The sputtered layer 104 in FIG. 8 is shown covering the entire outer surface of the transducer portion. However, the sputtered layer 104 only needs to be applied to the plane 120 so as to electrically connect the outer surface of the crystal cylinder and the outside lead 98. An electrical isolation layer 140, also referred to as a conformal coating, is then deposited over the outer surface of the transducer portion. The electrical isolation conformal layer 140 is preferably formed of a biocompatible non-attenuating coating, such as a UV curable adhesive material, for example DYMAX (TM) 20159 adhesive from Dymax Engineering Adhesives, Connecticut.

Referring back to FIG. 7, the construction of the probe body 84 is described. If desired, the probe body 84 may include a stiffener member 128 that extends from the probe body proximal end 86 to the probe body distal end 88. The stiffener member 128 prevents kinks in the probe body 84 in tight turns, as well as provides strength. The distal end 88 of the probe body is preferably attached to the transducer portion 92 by an adhesive layer 136.

As previously described, the second ends of the inside and outside lead central portions 119, 138 extend toward the probe body 84. After the stiffener member 128 is secured to the transducer portion 92 by the adhesive layer 136, the inside and outside lead central portions 119, 138 are twisted and extend to the second ends of the leads, which are coupled to the driving circuit of the probe through the connector 90. The twisting of the leads 96, 98 serves to reduce electrical noise to a minimum. A flat spring wire 132 is coiled around and surrounds the stiffener member 128 and twisted leads 96, 98.

The probe body 84 also includes a depth or zero alignment mark 134 on the outer surface of the probe body 84 near the proximal end. The depth mark 134 is visible through the extension tubes 16 of the catheter 10. The depth mark 134 is positioned such that the mark 134 is aligned with a predetermined location on the catheter extension tube 16 when the probe 82 is properly positioned within the catheter 10.

For purposes of reference only, the preferred dimensions of the ultrasound probe 82 are given. The outer diameter of the transducer 94 of the probe 82 is preferably approximately 0.040 to 0.047 inches, the wall thickness is preferably 0.010 inch, and the length is preferably 0.027 inch. The outer diameter of the probe body is preferably approximately 0.037 inches. In comparison, the probe lumen 36 has a diameter of approximately 0.056 inches. Therefore, the probe and transducer portion diameter is sufficiently small to allow the probe to fit within the first lumen 36 of the catheter 10, as well as to allow additional fluid flow through the first lumen 36 if required by the circumstances. The total length of the probe 82 is preferably approximately 79.75 inches. The length of the transducer portion 92 of the probe 82, including the matching layer and backing layer, is preferably approximately less than 0.5 inches.

In the preferred embodiment, the ultrasound probe of the present invention is used in connection with a system that includes a Doppler unit (not shown) and personal computer (not shown). The Doppler unit is used to drive the probe and to house the Doppler electronics. The personal computer is used to control the Doppler unit and display and process the signal data. The personal computer calculates the flow area using two components. The first component measures flow velocity and the second component measures flow area. The flow rate is a product of the two components.

Referring now to FIGS. 9 & 10, in the preferred embodiment of the ultrasound probe, the single cylindrical transducer 92 instantaneously analyzes the blood flow area and the blood flow velocity substantially simultaneously. It should be noted that the area and velocity are not measured precisely simultaneously in real time, but, as is known, the measurements are made essentially simultaneously, on the order of millionths of seconds. More specifically, the single cylindrical transducer 92 may be activated in two distinct modes instantaneously.

Each of the modes is activated at a different frequency. In the first mode for producing a beam for determining the area of the pulmonary artery for example, a frequency generator in the signal source 118B (FIG. 10) generates an 8 MHz signal in turn causing the transducer to generate an ultrasound signal in a radial direction, thereby creating a radially oriented signal beam 146 (FIG. 9). A standard frequency generator such as an Hewlett-Packard signal generator may be used to drive the transducer. In the second mode, for producing a beam for determining the blood velocity in the pulmonary artery for example, the frequency generator generates a 2 MHz signal in turn causing the transducer to generate an ultrasound signal in an axial direction, thereby creating an axially directed signal beam 144 (FIG. 9). The transducer crystal is preferably designed such that the optimum driving frequency for the radially directed beam 146 is 8 MHz while the optimum driving frequency for the axially directed beam 144 is 2.285 MHz. More specifically, for signal generator driving frequencies of 8 MHz and 2 MHz, respectively, the presently preferred transducer crystal dimensions are an outer diameter of 0.040–0.047 inch, a wall thickness of about 0.010 inch, and a length axially of about 0.027 inch. The difference between the respective driving frequencies and the transducer crystal design dimensions results in decoupling of the two driving signals for the preferred design. However, the transducer may be driven at other frequencies. When the transducer is driven at other frequencies, the transducer design is preferably modified so as to be optimized at the other frequencies, while preferably keeping the two frequencies for which the transducer is designed decoupled. The different dimensions may be determined by modeling.

The transducer crystal is preferably formed from PZT-5H, a formulation of Pb(Zr,Ti)O3 with high elctromechanical coupling coeffiecient and high dielectric constant.

The dimensions of the crystal are also designed to generate the axially or forwardly directed beam 144 in the shape of a wide cone. The wider the cone, the closer the velocity measurement is taken to the point where the area measurement is taken.

The radially oriented signal beam 146 is used to calculate the cross-sectional area of the blood flow. More specifically, the flow area is estimated by measuring the Doppler power in a narrow Doppler gate of predetermined area, Pn, for example one centimeter squared, and the power from a wider gate of an unknown area, Pw, which corresponds to the unknown flow cross-sectional area. The measured power from the wider gate Pw corresponds to the number of red blood cells insonified within the Doppler gate. The corresponding number of red blood cells insonified is proportional to the unknown cross-sectional area Pw. Therefore, if $$Pn = 1 \text{ cm}^2;$$

and $$Pw = x \text{ cm}^2$$

in order to calculate Pw, the unknown cross-sectional area, the following equation is used:

$$Pw/Pn = x \text{ cm}^2$$

In the second mode, the forwardly oriented signal beam 144 is used to calculate the blood particle velocity. The blood velocity is calculated directly from the Doppler frequency shift as measured by the forwardly oriented signal beam 144.

In order to eliminate the effect of the angle of incidence a between the axis of the transducer and the blood flow, the following equation is used to calculate the blood flow:

$$Q = V\cos(a) * (A/\cos(A))$$

wherein Q = blood flow; V = blood velocity; A = cross-sectional area; and a = angle of incidence between transducer axis and blood flow. In the equation for blood flow, the cos(a)'s cancel out, therefore eliminating the effect of the angle of incidence on the blood flow measurement. Because of the perpendicular nature of the radially and axially directed beams, the estimate of the volume flow would be self-compensating or independent of the orientation of the probe with the flow field.

By way of example, in one embodiment of the invention, the system personal computer screen displays the diameter mode signal echo pattern in M-mode, wherein the X-axis represents time, the Y-axis represents depth, and the Z-axis represents echo amplitude. Simultaneously, the second mode information, the velocity mode, is also preferably displayed in M-mode on the computer screen. Preferably the second mode display is color coded so as to clearly represent the speed of the moving blood particles.

Once the information is displayed on the screen, the user, referring to the first mode, marks the first echo nearest the probe, and the last Doppler signal furthest from the probe. These two measurements are used by the computer to determine the cross-sectional area. In the second mode, the velocity mode, the user marks the velocity wave. The mean blood flow velocity over the cardiac cycle is then calculated from this marked information.

The blood flow velocity and cross-sectional area are then calculated, using the above equation, so as to compute the blood flow. Therefore, the use of the distinct first and second modes of the single transducer element provide for an accurate blood flow measurement, while eliminating the effects of the angle of incidence between the transducer axis and the blood flow.

As previously described, the probe 82 is preferably designed for use with the multi-lumen catheter of the present invention. In addition to the previously described advantages of the multi-lumen catheter, the design of the catheter body 12 also provides the advantage of structural integrity. The configuration of the lumens and the thickness of the lumen walls contributes to the structural integrity and strength of the catheter body, thereby minimizing the possibility that the catheter may be constricted or crushed during use. More specifically, in the preferred embodiment of the invention, a substantial portion of each of the lumen walls preferably has a thickness greater than the shortest distance between the first wall of the probe lumen and the outer edge of the catheter body 12. Therefore, any possibility that the catheter body 12 may be pressed or any lumens may be constricted when the catheter is passed through a seal on an outer transport catheter is minimized.

Referring back to FIGS. 1-4, in a further preferred embodiment of the invention, a transport catheter includes the probe and injectate lumens 36 and 40, respectively but omits the inflation balloon and the inflation lumen. Omitting the inflation lumen allows the injectate lumen to be made larger if necessary by increasing the arcuate length or arcuate extent of the injectate lumen, thereby increasing its cross-sectional area and its flow characteristics. The catheter of this alternative preferred configuration has a number of applications, similar to those of the embodiment of FIG. 1, including sensing, fluid injection and sampling and the like. The probe lumen is still preferably circular in cross-section and occupies a substantial portion of the catheter cross-section. The injectate lumen is also preferably crescent shaped and occupies as much of the remaining cross-sectional area of the catheter as necessary to achieve high fluid flow in the lumen or to allow efficient introduction of more viscous fluids.

An alternative embodiment of a catheter 68 (FIG. 6) includes a first lumen exit port 70 proximal of the distal end of the catheter approximately 30 centimeters, in the embodiment where the catheter length is 110 centimeters. A round lumen plug 74 is sealed in the circular first lumen 76 to direct fluid from the first lumen externally of the catheter. The port 70 allows infusion of a fluid through the first lumen into the body cavity at a relatively high flow rate. The cross-sectional area of the port 70 is preferably the same as that of the first lumen. The cross-sectional configuration of the catheter is preferably the same as that shown in FIG. 2 to allow the relatively high fluid flow rates in the first lumen and in the injectate lumen, while also having a relatively small inflation lumen 78 and a relatively small fourth lumen. The injectate lumen 78 preferably has the same cross-sectional configuration as the preferred cross-sectional configuration of the injectate lumen 40 described above with respect to FIG. 2. A portion of the bottom surface 80 of the injectate lumen is shown as though the segmented sectional view of FIG. 6 were taken off center. In a preferred form of the catheter, thermistor wires from the fourth lumen cross over through the wall between the first and fourth lumens. The wires extend into the first lumen near the distal end of the catheter to a thermistor that is exposed to the outside of the catheter through the external wall of the first lumen.

Having thus described exemplary embodiments of the present invention, it should be noted by those skilled in the art that the within disclosures are exemplary only and that various other alternatives, adaptations and modifications may be made within the scope of the invention. Thus by way of example, but not of limitation, the position and shape of the outside lead may be modified while still having a substantial portion of the lead within the diameter defined by the outer surface of the crystal cylinders. Also the probe body portion of the probe may be designed with different materials then the stiffener member and flat spring, yet still satisfy the purpose and function of the probe body. Accordingly, it is to be understood that the present invention is not limited to the precise construction as shown in the drawings and described hereinabove.

We claim:

1. A method of measuring blood flow rate in a blood vessel by the use of an ultrasound probe, wherein the ultrasound probe includes a single hollow cylindrical transducer element comprising the steps of:

positioning the ultrasound probe in the vessel such that the distal end of the probe is at a desired location for measuring blood flow;

energizing the transducer element at a first frequency so as to generate a radially oriented signal beam;

energizing the transducer element at a second frequency so as to generate a forwardly oriented signal beam;

analyzing the radially generated signals to compute the cross-sectional area;

analyzing the forwardly generated signals to compute the velocity of the blood particles; and analyzing the cross-sectional area and blood velocity so as to compute the blood flow rate.

2. A method of measuring blood flow in accordance with claim 1 wherein the radially oriented signal beam and the axially oriented signal beam are generated simultaneously.

3. A method of measuring blood flow rate in accordance with claim 1 wherein the step of analyzing the radially generated signals includes the steps of:

processing the return Doppler signal from the radial beam;

determining the amplitude of the return Doppler signal;

calculating the number of red blood cells insonified as proportional to the return Doppler signal amplitude; and calculating the flow area by analyzing the number of red blood cells insonified.

4. A method of measuring blood flow rate in accordance with claim 1 wherein the step of analyzing the forwardly generated signals further comprises the steps of:

measuring the Doppler frequency shift from the forwardly generated signal beam;

computing the velocity from the Doppler frequency shift.

5. A method of measuring blood flow rate in accordance with claim 1 wherein the first frequency at which the transducer is energized is approximately eight megahertz.

6. A method of measuring blood flow rate in accordance with claim 1 wherein the second frequency at which the transducer is energized is approximately two megahertz.

7. A method of measuring blood flow rate in accordance with claim 1 wherein the forwardly oriented signal beam is generated in the form of a solid cone.

* * * * *